United States Patent [19]

Roizman et al.

[11] Patent Number: 4,554,159

[45] Date of Patent: Nov. 19, 1985

[54] VACCINE AND METHOD OF IMMUNIZING AGAINST HERPES SIMPLEX VIRUS (TYPES 1 AND 2)

[75] Inventors: Bernard Roizman, Chicago, Ill.; M. Robert Lang, Caluire et Cuire, France

[73] Assignee: Institute Merieux, Lyons, France

[21] Appl. No.: 320,760

[22] Filed: Nov. 12, 1981

[51] Int. Cl.⁴ ............................................. A61K 39/245
[52] U.S. Cl. ...................................... 424/89; 435/235
[58] Field of Search .................... 424/89; 435/235, 172

[56] References Cited

U.S. PATENT DOCUMENTS

| | | | |
|---|---|---|---|
| 3,897,549 | 7/1975 | Zygraich | 424/89 |
| 3,991,179 | 11/1976 | Beare et al. | 424/89 |
| 3,992,522 | 11/1976 | Chanock et al. | 424/89 |
| 4,009,258 | 2/1977 | Kilbourne | 424/89 |
| 4,029,763 | 6/1977 | Kilbourne | 424/89 |
| 4,147,772 | 4/1979 | Mc Aleer et al. | 424/89 |
| 4,206,287 | 6/1980 | Hannoun et al. | 424/89 |
| 4,278,662 | 7/1981 | Tobmann et al. | 424/89 |
| 4,317,811 | 3/1982 | Bertlord et al. | 424/89 |
| 4,322,404 | 3/1982 | Gauri et al. | 424/89 |
| 4,337,314 | 6/1982 | Oeschger et al. | 424/92 |
| 4,381,903 | 3/1982 | Tobmann et al. | 424/89 |

OTHER PUBLICATIONS

Murphy et al., Ann. N.Y. Acad. Sci., vol. 354, pp. 172-182 (1980).
Toplin et al., Virology, vol. 112, pp. 505-517 (1981).
Murphy et al., Infection and Immunity, vol. 37, No. 1, pp. 235-242 (Jul. 1982).
Morse et al., J. Virology, vol. 26, No. 2, pp. 384-410 (1978).
Morse et al., J. Virology, vol. 24, No. 1, pp. 231-248 (1977).
Aron et al., J. Virology, vol. 16, pp. 498-507 (1975).
Benyesh-Melnick et al., Cold Spring Harbor Symp. Quant. Biol., vol. 39, pp. 731-746 (1974).
Schaffer, Curr. Top. Microbiol. Immun., vol. 70, pp. 51-100 (1975).
Schaffer et al., pp. 595-617, In Huange et al. (ed.) Animal Virology, Plenum Publishing Corp., N.Y. (1976).
Marsden et al., J. Gen. Virol., vol. 31, pp. 347-372 (1967).
Subak-Sharpe et al., Cold Spring Harbor Symp. Quant. Biol., vol. 31, pp. 717-730 (1974).
Purifoy et al., Virology, vol. 68, pp. 374-386 (1975).
Pilarica et al., J. Gen. Virol., vol. 2, pp. 357-364 (1968).
Cassai et al., Intervirology, vol. 6, pp. 212-223 (1975/76).
Esparza et al., Virology, vol. 70, pp. 372-384 (1976).
Halperin et al., J. Pediatrics, vol. 97, pp. 91-93 (1980).
Smith et al., J. Mol. Biol., vol. 81, pp. 419-423 (1973).
Hayward et al., Proc. Nat. Acad. Sci. USA, vol. 72, No. 5, pp. 1768-1772; No. 11, pp. 4243-4247 (1975).
Hammer et al., J. Infect. Dis., vol. 141, No. 4, pp. 436-440 (1980).
Hill, pp. 241-244, In Andre et al., ed., Human Herpesvirus and Interdisciplinary Perspective, Elsevier, N.Y. (1981).
Hill et al., J. Gen. Virol., vol. 28, pp. 341-353 (1975).
Hill et al., J. Gen. Virol., vol. 47, pp. 205-207 (1980).
Hill et al., J. Gen. Virol., vol. 39, pp. 21-28 (1978).

Primary Examiner—Shep K. Rose
Attorney, Agent, or Firm—Wood, Dalton, Phillips, Mason & Rowe

[57] ABSTRACT

A live viral vaccine against herpes simplex virus types 1 and 2 (HSV-1 and HSV-2) incorporates as an effective ingredient at least one intertypic (HSV-1×HSV-2) vaccinal recombinant virus strain.

31 Claims, 4 Drawing Figures

BamHI digests

FIG. 1

Kpn I digests

RELATIONSHIP OF INFECTIVITY TO IMMUNOGENICITY OF RECOMBINANT HSV

VACCINE AND METHOD OF IMMUNIZING AGAINST HERPES SIMPLEX VIRUS (TYPES 1 AND 2)

BACKGROUND OF THE INVENTION

This invention relates to a live viral vaccine, a method of making the vaccine, and a method of immunizing a host against viruses. More specifically, this invention relates to a live viral vaccine, a method of making the vaccine and a method of immunizing against herpes simplex virus types 1 and 2 (HSV-1 and HSV-2, respectively) using the vaccine. The vaccine incorporates as an effective ingredient at least one intertypic (HSV-1×HSV-2) recombinant strain obtained by crossing selected strains of herpes simplex viruses.

Both distinguishable serotypes of herpes simplex virus (designated HSV-1 and HSV-2) cause infection and disease ranging from relatively minor fever blisters on lips to severe genital infections and generalized infections of newborns. Herpes simplex has increasingly been recognized as an etiologic agent in human encephalitis, and may be implicated in some human cancers.

Until now, no effective vaccine against herpes simplex viruses has been known.

SUMMARY OF THE INVENTION

It is an object of the invention to provide a live viral vaccine effective against disease-producing (wild type) HSV-1 and HSV-2, a method of making the vaccine and a method of immunizing a human host using the vaccine.

According to the invention, a live viral vaccine against HSV-1 and HSV-2 incorporates as its effective ingredient at least one avirulent intertypic (HSV-1×HSV-2) recombinant strain. The strains are obtained by crossing selected prototypic parental strains of HSV-1 and HSV-2 which have discriminating genetic markers, and progeny are selected on the basis of their desirable vaccinal characteristics.

The vaccinal strains are avirulent, stable (do not revert to the virulent state), provide demonstrated immunity to massive challenges of wild type strains of both HSV-1 and HSV-2, have low pathogenicity and disappear after immunization of a host.

Other characteristics and advantages of the invention will be apparent from the following detailed description taken in conjunction with the figures and the appended claims.

DETAILED DESCRIPTION OF THE INVENTION

Preliminary

In principle, viruses cause infected cells to produce specific proteins. These interact with each other and with cellular proteins, DNA or RNA to cause viral progeny to be made, to destroy the infected cell and to spread infection to previously noninfected cells. Some of these proteins also stimulate the host to produce antibody. HSV-1 and HSV-2 are related immunologically, but most of their proteins carry distinguishing marks (characteristics) which allow them to be differentiated. See Morse et al., "Anatomy of Herpes Simplex Virus (HSV) DNA: X. Mapping of Viral Genes by Analysis of Polypeptides and Functions Specified by HSV-1×HSV-2 Recombinants", *J. Virol.*, Vol. 26, No. 2 at 389–410 (May 1978), the disclosure of which is hereby incorporated by reference.

It is known from the formation of recombinant progeny that proteins of HSV-1 can interact with proteins of HSV-2 to form infectious progeny. It is also known that immunity to HSV infection is determined by host response to several proteins.

In accordance with this invention, it has been discovered that viral progeny of genetic recombinants of HSV-1 and HSV-2 are in general less virulent than wild type viruses because the degree of fit of interacting HSV-1 and HSV-2 proteins is less good than the degree of fit of HSV-1 alone or of HSV-2 alone. Also, because recombinants are a mixture of genes they protect against both HSV-1 and HSV-2 infection, if judiciously selected.

Recombinants differ in principle from viruses which are differentiated by mutagenesis to cause them to lose their ability to produce disease. In most instances, mutagenesis involves the substitution of one or more base pairs; it does not usually involve the replacement of one gene by another and such mutants can easily mutate (revert) to wild type phenotype (i.e. become virulent again).

Recombinants cannot revert to virulence because entire genes and clusters of genes have been substituted. In addition, mutants contain antigenic determinants to only one virus serotype. As indicated above, and disclosed in detail below, recombinants can be selected to contain antigenic determinant sites to both HSV-1 and HSV-2.

Therefore, in accordance with the invention, a live viral vaccine effective against both HSV-1 and HSV-2 is provided by preparing recombinant progeny of prototypical parental HSV-1 and HSV-2 strains which are selected on the basis of their ability to be distinguished from the recombinants. Thus, the parental strains are those carrying discriminating genetic markers which allow identification and isolation of recombinants. As a result, the parental strains are crossed in such a way as to produce recombinants which are distinguishable and isolatable from the parents on the basis of the distinguishing characteristics of the parents.

The distinguishing characteristics of the parents need not be related to the vaccinal characteristics of the recombinants.

The attenuated recombinants are selected on the basis of their immunogenicity, avirulence, lack of tendency to revert to virulence, and tendency to disappear from the host after immunization. These characteristics of specific recombinants are readily empirically determined.

The invention contemplates the discovery that crossing of prototypical parental strains which carry discriminating markers significantly enhances the frequency of the production of vaccinal recombinants and allows isolation thereof. The invention further contemplates the discovery that attenuated intertypic (HSV-1×HSV-2) recombinant strains retain their attenuation with respect to wild type HSV-1 and HSV-2.

Thus, the invention provides a live viral vaccine, a method of making the vaccine, and a method of immunizing a human host against both HSV-1 and HSV-2 using the vaccine.

While the invention is described below in detail with respect to eight preferred vaccinal strains selected from twenty-eight specific recombinants obtained by crossing several parental HSV-1 and HSV-2 strains, the details of the following disclosure are not intended to be limiting but, rather, are offered for exemplification and clearness of understanding only.

Description of the Preferred Embodiments

Morse et al., "Anatomy of Herpes Simplex Verus DNA: IX. Apparent Exclusion of Some Parental DNA Arrangements in the Generation of Intertypic (HSV-1×HSV-2) Recombinants", *J. Virol.*, Vol. 24, No. 1 at 231-48 (October 1977), and hereafter referred to as "Morse et al. (1977)", the disclosure of which is hereby incorporated by reference, describes the preparation and characterization of 28 recombinants produced by crossing selected parental herpes simplex viruses types 1 and 2 (HSV-1 and HSV-2, respectively).

The parental crosses described in Morse et al. are of two kinds. In the first, temperature-sensitive mutants of HSV-1 and HSV-2 were crossed to produce wild type recombinants. In the second, temperature-sensitive mutants of HSV-1 rendered resistant to phosphonoacetic acid (PAA) were crossed with wild type HSV-2, and recombinants that multiplied at nonpermissive temperature and were resistant to PAA were selected.

The DNAs of the recombinants were mapped with one or more of various restriction endonucleases.

It has now been found that at least eight of the 28 recombinant strains described in the Morse et al. (1977) article are safe and effective for use as effective ingredients of a vaccine for immunizing a human host against both HSV-1 and HSV-2. More specifically, the exemplified strains of interest are avirulent, exhibit the desirable characteristics of immunogenicity and latency, and also exhibit a low level of pathogenicity. Further, it is believed that the strains lack oncogenicity.

Eight vaccinal recombinant strains, which are examples of preferred strains of the invention, have been deposited with the American Type Culture Collection (ATCC), Rockville, Md. 20852 (USA), and are identified by the following designations used in the Morse et al. (1977) article, and by corresponding ATCC accession numbers:

| Strain Designation | ATCC Accession No. |
|---|---|
| A5C | VR 2019 |
| D4E1 | VR 2020 |
| D4E3 | VR 2021 |
| C7D | VR 2022 |
| D3E2 | VR 2023 |
| C5D | VR 2024 |
| D5E1 | VR 2025 |

| Strain Designation | ATCC Accession No. |
|---|---|
| D1E1 | VR 2026 |

Preparation of Recombinants

The parental virus strains of the eight exemplary strains, identified above, of the Morse et al. (1977) article are as follows:

(a) HSV-1 (KOStsE6), a DNA$^+$ts mutant described at Aron, G. M. et al., "DNA Synthesis and DNA Polymerase Activity of Herpes Simplex Virus Type 1 Temperature-Sensitive Mutants", *J. Virol.* 16:498–507 (1975); Benyesh-Melnick, M. et al., "Viral Gene Functions Expressed and Detected by Temperature-Sensitive Mutants of Herpes Simplex Virus", *Cold Spring Harbor Symp. Quant. Biol.* 39:731–746 (1974); Schaffer, P. A., "Temperature-Sensitive Mutants of Herpesviruses", *Curr. Top. Microbiol. Immunol.* 70:51–100 (1975); and Schaffer, P. A. et al., "Genetics of Herpesviruses", p. 546-617, In A. Huange, D. Baltimore, and C. Fred Fox (ed.), *Animal Virology*, Plenum Publishing Corp., New York (1976), the disclosures of which are hereby incorporated by reference;

(b) HSV-1 (17tsJ), a DNA$^-$ts mutant whose properties have been described at Marsden, H. S. et al., "Control of Protein Synthesis in Herpesvirus-Infected Cells: Analysis of the Polypeptides Induced by Wild Type and Sixteen Temperature-Sensitive Mutants of HSV Strain 17", *J. Gen. Virol.* 31:347–372 (1976); and Subak-Sharpe, J. H. et al., "Genetic and Biochemical Studies with Herpesvirus", *Cold Spring Harbor Symp. Quant. Biol.* 31:717–730 (1974), the disclosures of which are hereby incorporated by reference;

(c) HSV-1 (HFEMtsN102), a known DNA$^-$ mutant obtained from Alexander Buchan, Department of Medical Microbiology, University of Birmingham, England;

(d) HSV-2 (186tsB5), a DNA$^-$ts mutant described at Benyesh-Melnick, M. et al., "Viral Gene Functions Expressed and Detected by Temperature-Sensitive Mutants of Herpes Simplex Virus", *Cold Spring Harbor Symp. Quant. Biol.* 39:731–746 (1974); Purifoy, D. J. M. et al., "DNA Polymerase Induction by DNA-Negative Temperature-Sensitive Mutants of Herpes Simplex Virus Type 2", *Virology* 68:374–386 (1975); and Schaffer, P. A., "Temperature-Sensitive Mutants of Herpesviruses", *Curr. Top. Microbiol. Immunol.* 70:51–100 (1975), the disclosures of which are hereby incorporated by reference;

(e) HSV-2 (186), the known parent strain of HSV-2 (186tsB5) described at Ejercito et al., "Characterization of Herpes Simplex Virus Strains Differing in Their Effects on Social Behavior of Infected Cells", *J. Gen. Virol.* 2:357–364 (1968), the disclosure of which is hereby incorporated by reference; and (f) HSV-2 (GP6), a syn$^-$ mutant obtained from HSV-2 (G) and described at Cassai et al., "Plaque Dissociation of Herpes Simplex Viruses: Biochemical and Biological Characters of the Viral Variants", *Intervirology* 6:212–223 (1975), the disclosure of which is hereby incorporated by reference.

Two basic selection schemes are used to obtain intertypic recombinants in the Morse et al. (1977) article. The first involves infection with ts mutants of HSV-1 and HSV-2 and selection for progeny capable of growing at nonpermissive (ts+) temperatures, as described at Esparaza, J. et al., "Intertypic Complementation and Recombination Between Temperature-Sensitive Mutants of Herpes Simplex Types 1 and 2", *Virology* 70:372-384 (1976), as modified by Morse et al. (1977), above. The disclosure of the Esparaza et al. article is hereby incorporated by reference. The second selection scheme entails selection of ts+ PAA$^r$ progeny from cells doubly infected with a wild type HSV-2 and an HSV-1 ts− PAA$^r$ mutant.

Three series of intertypic recombinants were prepared by infecting cells with the selected strains of HSV-1 and HSV-2 containing genetic markers as shown in Table I, below:

TABLE I
PHENOTYPE AND BIOLOGICAL PROPERTIES OF PARENTAL STRAINS AND INTERTYPIC RECOMBINANTS[a]

| Series | Parental Strains and Phenotypes HSV-1 | HSV-2 | Recombinant phenotype selected | Recombinant designation | Plaque morphology in vero cells | Efficiency of plating 38.5° C./ 33.5° C. |
|---|---|---|---|---|---|---|
| A | 17tsJ (ts−PAA$^r$syn+) | GP6 (ts+PAA$^s$syn−) | ts+PAA$^r$ | A5C | syn+ | 0.01 |
| C | HFEMtsN102 (ts−PAA$^r$syn−) | 186 (ts+PAA$^s$syn+) | ts+PAA$^r$ | C5D | syn− | 0.003 |
|   |   |   |   | C7D | syn− | 0.75 |
| D | KOStsE6 (ts−PAA$^s$syn+) | 186tsB5 (ts−PAA$^s$syn+) | ts+PAA$^s$ | D1E1 | syn+ | 0.01 |
|   |   |   |   | D3E2 | syn+ | *b |
|   |   |   |   | D4E1 | syn+ | * |
|   |   |   |   | D4E3 | syn+ | 4.0 |
|   |   |   |   | D5E1 | syn+ | 1.0 |

[a] ts−,ts+, Temperature-sensitive and wild-type phenotypes, respectively. PAA$^r$, PAA$^s$ Genotypes conferring resistance and sensitivity to PAA. syn−, Strain capable of inducing syncytial plaque morphology due to the fusion of indicator cells to form polykaryocytes; syn+, virus has wild-type plaque morphology, i.e., plaques characterized by clumps of rounded cells.
[b] Plaques small at 38.5° C. and not readily seen at 33.5 C.

The doubly infected Vero cells were incubated at 33.5° C. for 18 to 20 hr. The progeny was then plated under agarose overlay and incubated at nonpermissive temperature (38.5° C.). The progenies of series A and C were plated under overlay containing PAA (100 μg/ml).

The A and C series were prepared by crossing an HSV-1ts parent made PAA$^r$ with ts+ strains of HSV-2. Thus, in all instances, the progenies were selected for ts+PAA$^r$.

The selected progeny was then analyzed for expression of the syn marker. In series A, the HSV-2 strain expressed syncytial plaque morphology (syn−), whereas in series C, the HSV-2 strain was nonsyncytial (syn+). All crosses in series A and C were done at a multiplicity of 3 PFU/cell of each parent.

The D series was prepared by crossing ts parents and selecting for the ability of the progeny to grow at nonpermissive temperature as reported by Esparaza et al., above.

Recombinants were isolated by picking plaques from infected monolayers overlaid with agarose and incubated under selective conditions. In series A and C, plaque isolates of the initial cross were plaque-purified repeatedly under selective conditions before stocks were prepared. In preliminary experiments it was observed that approximately 0.5 to as much as 3% of the progeny of doubly infected cells plated under selective conditions. However, the progeny of many of the isolated plaques segregated upon further passage into parental types or a parental type and recombinants.

Some segregants were readily demonstrable upon cultivation of progenies of individual plaques under selective and nonselective conditions. Other segregants were identified by analyses of the plaque morphology in HEp-2 cells. In some instances, the presence of parental and recombinant progeny became manifest only after digestion with endonucleases in that both parental and recombinant fragments were present in the same gel.

In series D, virus stocks were prepared under nonselective conditions after the second or third plaque purification. Consequently, the progeny selected on subsequent recloning might have arisen from additional rounds of recombination.

Further details of the procedure for preparing the recombinations are set forth in the Morse et al. (1977) article identified and incorporated by reference, above.

Designation of Recombinants

Each recombinant was designated according to parental cross (series A, C or D), initial clone number (1, 2, etc.) and number of plaque purifications (A, B, etc.). In some instances, segregation of a mixture of recombinants did not occur until after several plaque purifications, and these were designated by an additional arabic number.

Characterization of Recombinants

As described in Halperin et al., "DNA Fingerprinting in Investigation of Apparent Nosocomial Acquisition of Neonatal Herpes Simplex", *J. Pediatrics* 97:91-93 (1980), the disclosure of which is hereby incorporated by reference, digestion of viral DNA, and subsequent analysis of resulting fragments by gel electrophoresis, is useful in characterizing viral DNA (DNA mapping) as well as in providing a unique "fingerprint" for any given virus.

Figure 1:
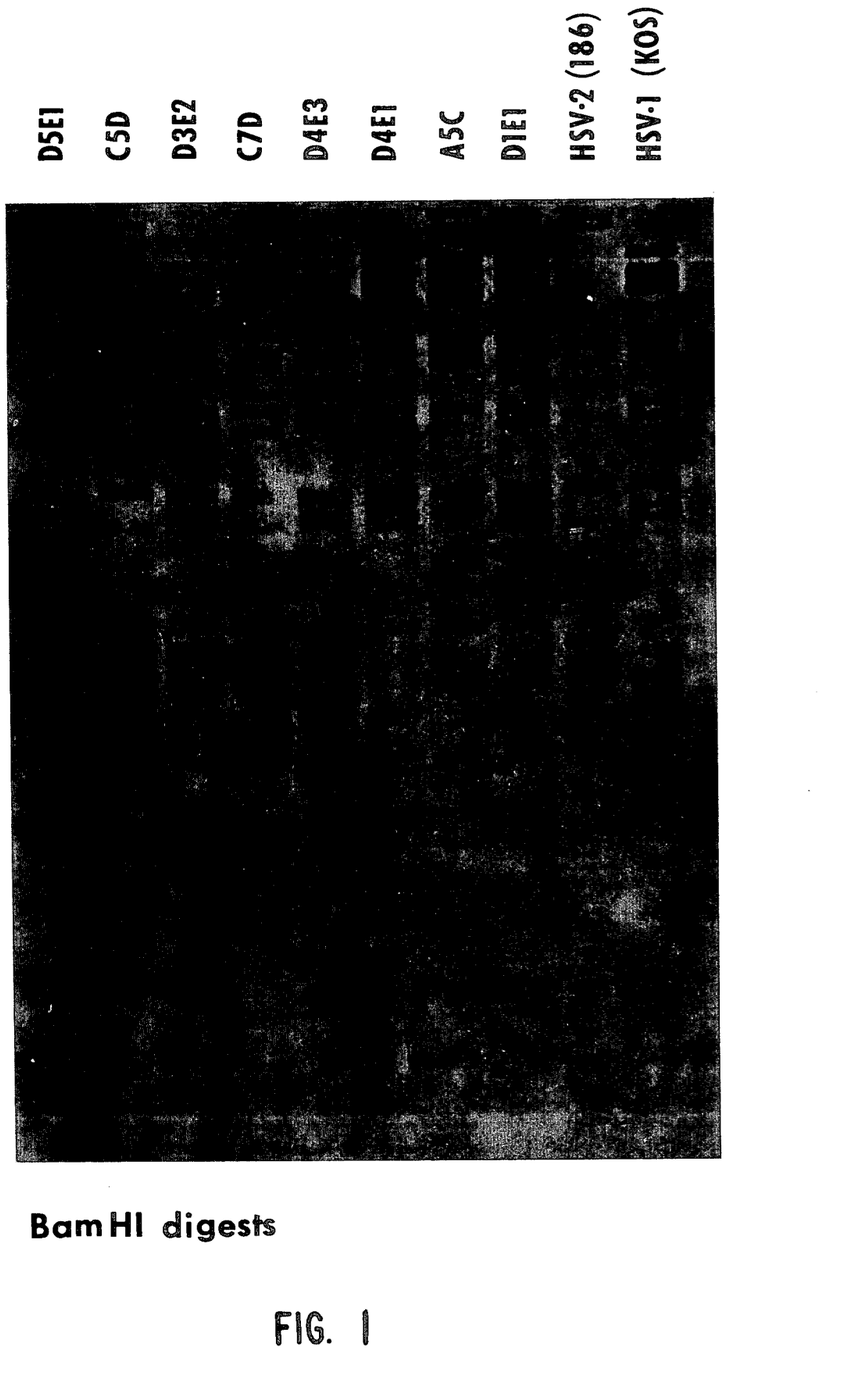
FIG. 1 is an electrophoretic profile of the DNAs of exemplary HSV-1×HSV-2 recombinant strains of the invention digested with BAM H1 restriction endonuclease, with the digested wild type virus DNAs of HSV-1 (KOS) and of HSV-2 (186) shown as references.
Figure 2:
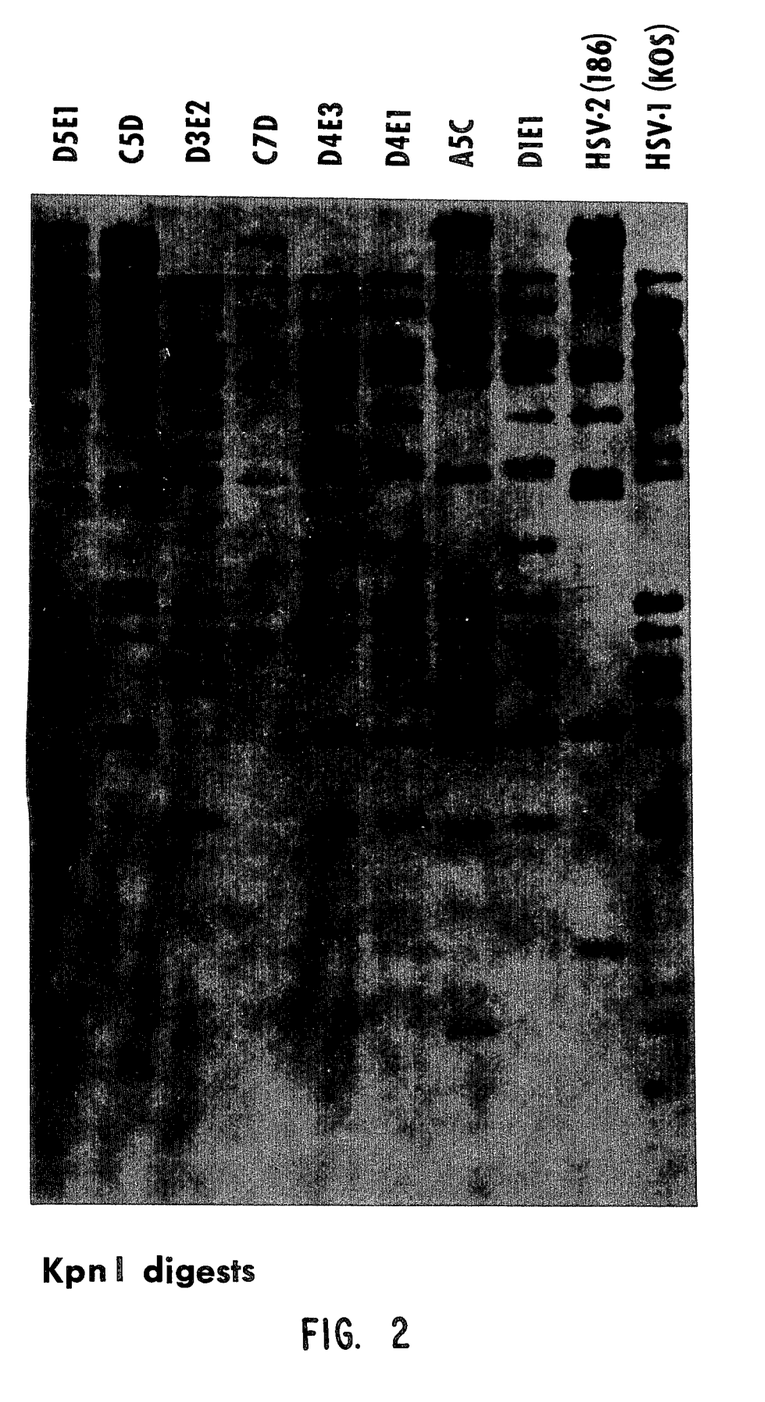
FIG. 2 is an electrophoretic profile of the DNAs of exemplary HSV-1×HSV-2 recombinant strains of the invention digested with Kpn 1 restriction endonuclease, with the digested wild type virus DNAs of HSV-1 (KOS) and HSV-2 (186) shown as references.

FIGS. 1 and 2 are electrophoretic profiles of the DNAs of the exemplary HSV-1 and HSV-2 recombinant strains of the invention, digested with the restriction endonuclease Bam H1 or Kpn 1, respectively, subjected to electrophoresis in agarose gels, and then stained with ethidium bromide. In each of FIG. 1 and FIG. 2, the DNAs of wild type HSV-1 (KOS) and of wild type HSV-2 (186), serve as references.

The profiles of FIGS. 1 and 2 were obtained according to procedure of Example 1, below.

EXAMPLE 1

Characterization of Recombinant DNA by Digestion with Restriction Endonucleases

Restriction endonucleases are designated herein according to the nomenclature of Smith and Nathans, "A Suggested Nomenclature for Bacterial Host Modification and Restriction Systems and Their Enzymes", *J.*

Mol. Biol. 81:419 (1973), the disclosure of which is hereby incorporated by reference. Bam H1 and Kpn 1 were prepared from appropriate cell pastes by standard purification procedures: precipitation of DNA (streptomycin sulfate), fractionation of protein (ammonium sulfate), molecular sieve chromatography (agarose beads), and ion exchange chromatography (phosphocellulose). The restriction endonuclease preparations were shown to be free of contaminating exo- or endonuclease activity before use.

The DNA was cleaved with each restriction endonuclease by incubation for 2 hr. at 37° C. in a total volume of 100 to 200 μl. For digestion with Bam H1 or Kpn 1, the mixtures contained 20 mM Tris (pH 7.5), 20 mM $MgCl_2$, and 20 mM NaCl. The reaction was stopped by the addition of 60 mM EDTA. Sucrose (20 μl, 60% [wt/wt]) containing bromophenol blue was also added to the reaction mixture at this time.

The DNA fragments in the limit digests were separated by electrophoresis through slab gels (20×20 cm) containing 0.8% agarose (Seakem, Marine Colloids, Inc., Rockland, Md.) for 18 hr. at 2.25 V/cm in Tris-phosphate buffer (30 mM $NaH_2PO_4$, 36 mM Tris, 1.0 mM EDTA, pH 8.0) as described in Hayward, G. S. et al., "The Anatomy of Herpes Simplex Virus DNA: Strain Difference and Heterogenicity in the Location of Restriction Endonuclease Sites", Proc. Natl. Acad. Sci. U.S.A. 72:1768–1772 (1975); and Hayward, G. S. et al., "Anatomy of Herpes Simplex Virus DNA: Evidence for Four Populations of Molecules that Differ in the Relative Orientations of Their Long and Short Segments", Proc. Natl. Acad. Sci. U.S.A. 72:4234–4247 (1974), the disclosures of which are hereby incorporated by reference, except that electrophoresis was done with slabs rather than with tubes. After electrophoresis, the gels were dried on Whatman No. 1 filter paper. Autoradiograms were made on Cronex Medical X-ray film.

Immunogenicity and Virulence

The following examples set forth test procedures and results demonstrating the virulence and immunogenicity of the exemplary recombinant strains of the invention in comparison to the characteristics of the parental strains and wild type HSV-1 and HSV-2.

EXAMPLE 2

Evaluation of Virulence

Each of the eight exemplary recombinant viruses of the invention, as well as the parental strains and various wild type HSV-1 and HSV-2 strains, were serially tenfold diluted in phosphate buffer, saline and glucose (0.1%). Inactivated calf serum (1%) was used as a diluent. Prior to dilution, the virus stocks were stored at −70° C. in admixture with skim milk.

Balb/C mice (4–6 weeks old) were obtained from the same supplier and were randomly distributed in groups of 20. Each group consisted of 10 males and 10 females, housed separately, and each group was individually identified with a respective strain.

Regardless of the inoculation or challenge route used (i.e. intracerebral, intraperitoneal or subcutaneous), the tests were conducted by injecting one group of 20 mice with each of the dilutions of viruses, from $10^0$ (undiluted virus harvested from cell cultures) to $10^{-8}$ (except for F and G wild type strains where dilutions of $10^{-3}$ through $10^{-8}$ only were used). Two control groups were injected with diluent for each test.

F and G wild type strains are described at Ejercito et al., above. MGH10 is a highly virulent wild type strain isolated from a case of encephalitis at Massachusetts General Hospital, and is described at Hammer et al., "Temporal Cluster of Herpes Simplex Encephalitis: Investigation by Restriction Endonuclease Cleavage of Viral DNA", J. Infect. Dis. 141: 436–440 (1980), the disclosure of which is hereby incorporated by reference.

The infectivity titer of each viral suspension was determined with the dilutions of the viruses used above by plaque counting on Vero cells.

After inoculation, mice were checked daily for 20 days and subsequently checked twice a week up to the 50th day, or as otherwise stated, past infection. The inoculation procedures are summarized as follows.

For intracerebral inoculation, mice were anesthetized by using ether or an intraperitoneal injection of pentobarbitone.

Each mouse received 50 μl of the virus dilutions or of the diluent in the right hemisphere of the brain.

For intraperitoneal inoculation, each mouse received 0.2 ml, without anesthesia.

For subcutaneous inoculation, mice were injected in the left foot pad with 20 μl, without anesthesia.

Figure 3:
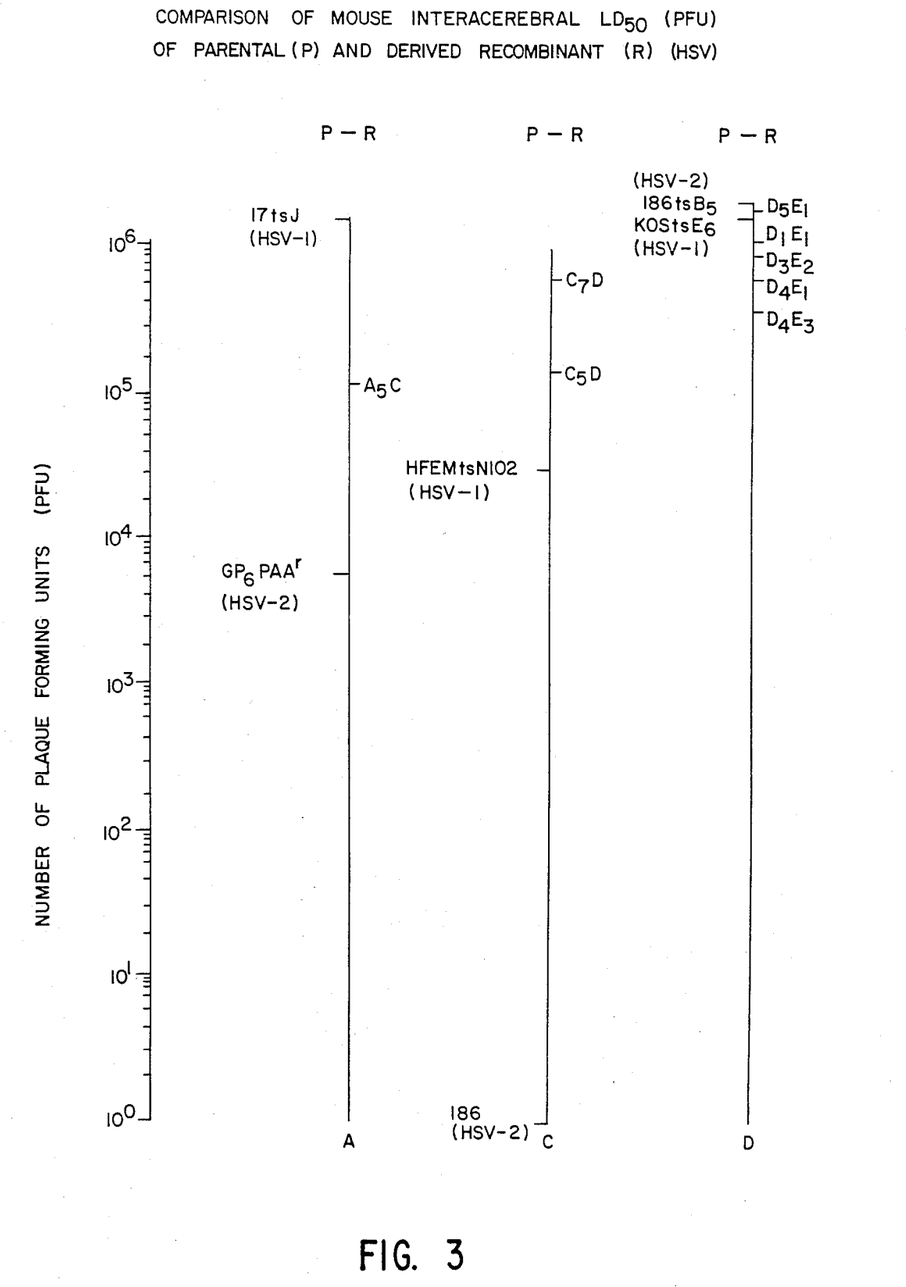
FIG. 3 is a comparison of mouse intracerebral $LD_{50}$ of parental and derived recombinant HSV of the invention.

FIG. 3 is a summary of the test results comparing mouse intracerebral $LD_{50}$, measured in plaque-forming units (PFU) of the parental and derived recombinant HSV of the invention. The logarithmic scale at the left of the figure designates the number of PFU required to kill 50% of test animals via intracerebral injection. The three series of parental and recombinant strains are designated A, C and D, and the number of PFU required to kill 50% of the test animals for each parental strain and each of the eight recombinant strains of the invention are indicated.

In several instances, it appears that the $LD_{50}$ for given mutant parent strains are higher than for corresponding recombinants. The lack of virulence in such cases is due entirely to temperature sensitive lesions in as much as the temperature of the mouse is at or near the temperature at which the temperature-sensitive virus does not multiply.

Since mutants readily revert and are able to multiply at higher temperatures, and since revertants reacquire the virulent properties of the parent viruses, such mutants are not suitable for vaccines.

Because recombinants are "wild type" with respect to temperature properties and because they have exchanged genetic information, none of the recombinants can reacquire the genetic information or the properties of the wild type viruses. Hence, their properties are stable.

Based on the distribution of deaths, a calculation of the lethal dose 50% ($LD_{50}$) was made for each test. In order to compare the different strains, the number of $LD_{50}$ per ml of virus was then referred to the infectivity titer (plaque-forming units per ml). (In all tests, calculation of either virulence, or immunity of infectivity titers were done by the well-known Kärber method.) The final results are expressed as log PFU per $LD_{50}$, shown in Table II, below.

TABLE II

PATHOGENICITY
Virulence is expressed as log PFU/1 lethal dose 50%.

| | Inoculation Route | | |
|---|---|---|---|
| | IC | IC Expt.* | IP |
| Strains | 1 | 2 | 2 |
| D5E1 | 7.8 | 7.7 | 8.9 |
| D4E1 | 7.6 | | |
| D3E2 | 7.5 | 6.9 | 8.6 |
| D4E1 | 6.8 | | |
| G | 0.7 | | |
| F | 3.9 / 2.5 | 1.5 | 5.9 |

*Two experiments were conducted at different times.

EXAMPLE 3

Evaluation of Immunogenicity

Mice which survived the virulence test (Example 2, above) were considered to be immunized with various amounts of virus. Their immunities were assayed with a uniform amount of challenge viruses on the 50th day after the virulence test.

The virus suspensions used for challenging the mice were titered for virulence on 4–6 week old Balb/C mice using the intracerebral route.

For challenging, appropriate virus dilutions in phosphate-buffered saline, glucose and inactivated calf serum were prepared in order to have 3,000 lethal doses in 50 μl. The infectivity titers were checked simultaneously.

Inoculations were carried out in the same manner as in Example 2, above. Mice were then observed daily for 20 days, and subsequently twice a week up to the 30th day.

The intracerebral challenge route was selected because the brain is the most sensitive organ of the body, in terms of the disease producing or killing effects of the virus.

Thus, in view of the sensitive intracerebral inoculation and challenge route, the results strongly reflect the attenuated properties of the vaccinal recombinants, leading to the conclusion that the method of the invention provides a means for providing strains whose properties are attenuated such that they provide immunization without causing disease or death.

Based on the distribution of survivors after the challenges, calculations of the protective dose 50% ($PD_{50}$) of the strains used for the virulence test were made for each test. The $PD_{50}$ was then referred to the infectivity titer, as in Example 2, above. The final results are expressed as log PFU per $PD_{50}$ in Table III, below.

TABLE III

IMMUNIZATION
All challenges were by IC route. Immunogenicity is expressed as log PFU/1 Protective Dose 50%

| F | MGH10 | G | MGH10 | G | | Challenge Strain Immunization Route |
|---|---|---|---|---|---|---|
| | IC | | | IP | | |
| | | | | | | Expt.* |
| 1 | 2 | 1 | 1 | 2 | 2 | Imm. Strain |
| 4.5 | 3.1 | 3.5 | 2.9 | 7 | 6.2 | D5E1 |
| 3.1 | | 2.6 | | | | D4E1 |

TABLE III-continued

IMMUNIZATION
All challenges were by IC route. Immunogenicity is expressed as log PFU/1 Protective Dose 50%

| F | MGH10 | G | MGH10 | G | | Challenge Strain Immunization Route |
|---|---|---|---|---|---|---|
| | IC | | | IP | | |
| | | | | | | Expt.* |
| 1 | 2 | 1 | 1 | 2 | 2 | Imm. Strain |
| 2.9 | 2.1 | 1.9 | 2.8 | 7 | 6.8 | DE32 |
| 3.8 | | 4.2 | | | | D1E1 |
| (1) | | 0.7 | | | | G |
| (0.9) | 1 | (0.6) | 0.6 | 6.3 | 4.5 | F |
| 1.6 | | 1 | | | | |

*Two experiments were conducted at different times.

EXAMPLE 4

Evaluation of Immunogenicity

Table IV summarizes the immunogenicity resulting from intracerebral infection of host animals with each of three recombinant strains D5E1, D1E1 and D3E2. The host animals (4–6 week old Balb/C mice) were challenged 120 days after immunization with known wild type HSV-1 and HSV-2 viruses designated WT17 and 186, respectively. (WT17 is described in the Marsden et al. paper, above. 186 is described in the Esparaza et al. article, above.)

In each case, different groups of mice were immunized with 10,000 and, in the case of D1E1 and D3E2, 100,000 PFU of the respective strains via the intracerebral route, following the procedure of Example 2, above. Controls were non-immunized.

After 120 days, each group was challenged with 3,000 $LD_{50}$ and, in some cases, 30,000 $LD_{50}$ of HSV-1 or HSV-2, and the number of survivors after 30 days were measured.

TABLE IV

SURVIVORS OF I.CER. INFECTION WITH RECOMBINANT VIRUS RESIST A SUBSEQUENT CHALLENGE WITH WILD TYPES 1 & 2 HSV

| I. Cer. Immunization | | I. Cer. Challenge - 120 Days | | |
|---|---|---|---|---|
| Strain | Dose (PFU) | Strain | Dose ($LD_{50}$) | Survival |
| D5E1 | 10,000 | Type-1 | 3,000 | 5/5 |
| D5E1 | 10,000 | (WT-17) | 30,000 | 5/5 |
| D5E1 | 10,000 | Type-2 | 3,000 | 5/5 |
| D5E1 | 10,000 | (186) | 30,000 | 5/5 |
| D1E1 | 10,000 | Type-2 | 3,000 | 3/5 |
| D1E1 | 100,000 | (186) | 3,000 | 5/5 |
| D3E2 | 10,000 | Type-2 | 3,000 | 5/5 |
| D3E2 | 100,000 | (186) | 3,000 | 3/5 |
| Controls | — | Type-1 | 3,000 | 0/5 |
| Controls | — | Type-1 | 30,000 | 0/5 |
| Controls | — | Type-2 | 3,000 | 0/5 |
| Controls | — | Type-2 | 30,000 | 0/5 |

Table V summarizes the number of animals immunized by intracerebral infection with various doses of the recombinant strains, and surviving a challenge 60 days after immunization with a dose of 3,000 $LD_{50}$ of either of strains WT17 or 186 of HSV-1 and HSV-2, respectively.

TABLE V

SURVIVORS OF I.CER. INFECTION WITH RECOMBINANT VIRUSES RESIST A SUBSEQUENT I. Cer. CHALLENGE WITH WILD TYPE HSV

| I. Cer. Immunization | | I. Cer. Challenge - 60 days | | |
|---|---|---|---|---|
| Strain | Dose (PFU) | Dose (LD$_{50}$) | 186 | WT17 |
| D1E1 | $1 \times 10^{3.2}$ | 3,000 | 3/5 | 5/5 |
| D3E2 | $1 \times 10^{3}$ | " | 4/5 | 5/5 |
| D4E1 | $1 \times 10^{2.8}$ | " | 5/5 | 5/5 |
| D5E1 | $1 \times 10^{3.5}$ | " | 5/5 | 5/5 |
| C7D | $1 \times 10^{3.6}$ | " | 3/5 | 5/5 |
| C5D | $1 \times 10^{2.2}$ | " | 4/5 | 5/5 |
| D4E3 | $1 \times 10^{5.5}$ | " | 4/5 | 4/4 |
| D4E3 | $1 \times 10^{4.5}$ | " | 5/5 | 5/5 |
| D4E3 | $1 \times 10^{3.5}$ | " | 5/5 | 5/5 |
| D4E3 | $1 \times 10^{2.5}$ | " | 5/5 | 5/5 |
| Wild Type Controls | — | — | 0/5 | 0/5 |

Table VI illustrates the effect of intraperitoneal vaccination with strain D5E1 on resistance of test animals to intracerebral challenge with wild-type HSV-2(G). A group of mice were vaccinated intraperitoneally with 10 or 10,000 PFU of recombinant strain D5E1, and challenged at 67 days by intracerebral injection of wild-type HSV-2(G).

TABLE VI

EFFECT OF I.PER. VACCINATION ON RESISTANCE TO I. CER. CHALLENGE

| Strain | I.P. Immunizing Dose (PFU) | HSV-2 I.C. Challenge at 67 Days | |
|---|---|---|---|
| | | Dose (PFU) | Survivors/Tested |
| Wild Type | None | 30 | 1/11 |
| HSV-2(G) | None | 300 | 0/10 |
| Recomb. | 10 | 30 | 2/9 |
| D5E1 | 10,000 | 300 | 0/10 |
| | | 30 | 8/10 |
| | | 300 | 1/10 |

Table VII illustrates the effect of intraperitoneal vaccination with strains D5E1 and A5C on resistance of test animals to subsequent intraperitoneal challenge with wild-type HSV-2(G). Two groups were vaccinated intraperitoneally with 10,000 PFU of recombinant strains D5E1 or A5C and subsequently challenged with various doses of wild-type HSV-2(G).

TABLE VII

EFFECT OF I.PER. VACCINATION ON RESISTANCE TO I. PER. CHALLENGE

| Strain | I.P. Immunizing Dose (PFU) | HSV-2 I. Per. Challenge at 67 Days | |
|---|---|---|---|
| | | Dose (PFU) | Survivors/Tested |
| Wild Type | None | 30 | 3/5 |
| HSV-2(G) | " | 300 | 3/5 |
| | " | 500 | 3/5 |
| | " | 1,000 | 3/5 |
| | " | $2.5 \times 10^7$ | 0/5 |
| | " | $1.5 \times 10^8$ | 0/5 |
| D5E1 | 10,000 | 30 | 10/10 |
| | " | 300 | 10/10 |
| A5C | 10,000 | $2.5 \times 10^7$ | 3/9 |
| | " | $1.25 \times 10^8$ | 6/10 |

Figure 4:
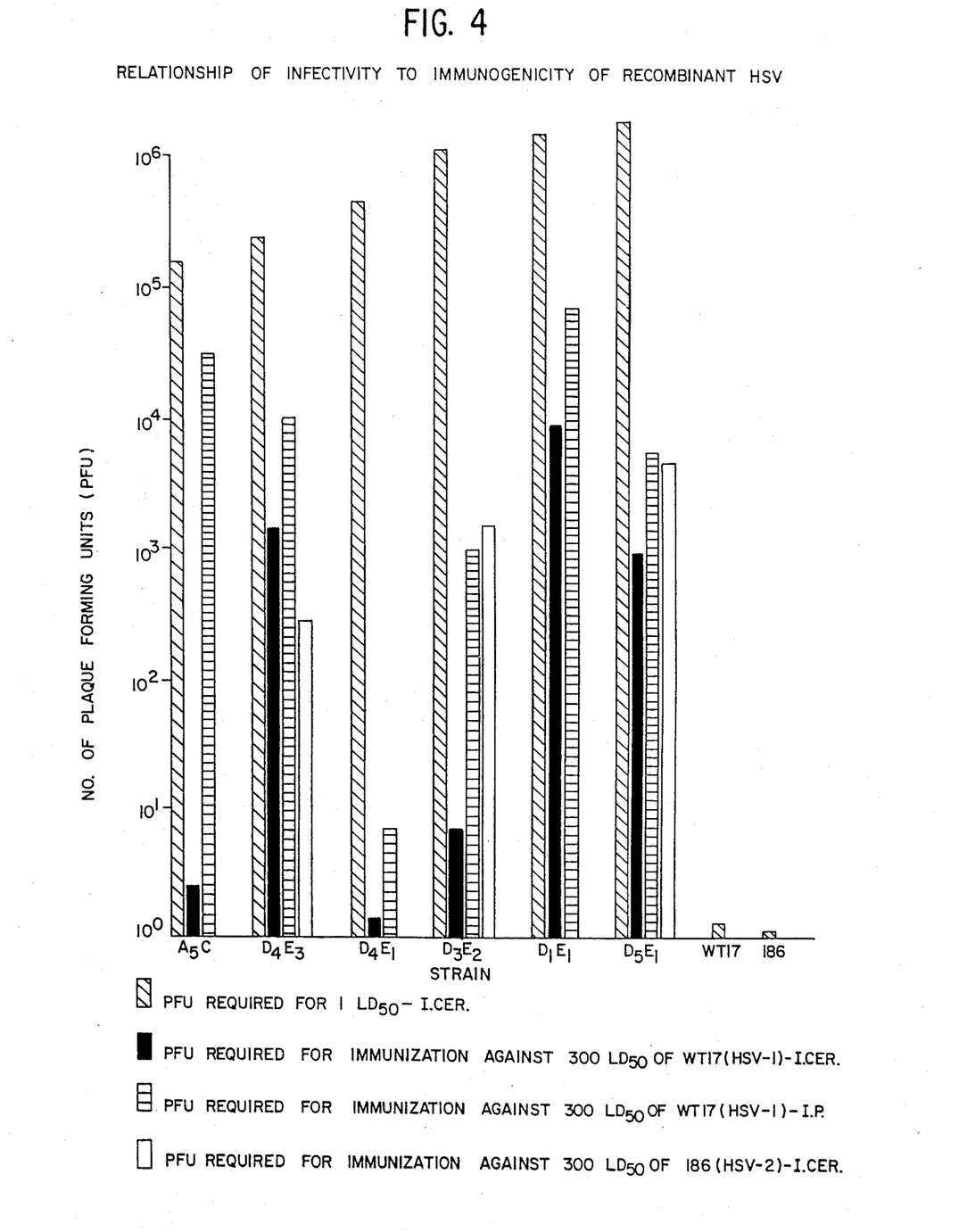
FIG. 4 is a summary of the relationship of infectivity to immunogenicity of recombinant HSV, with wild type HSV-1 and HSV-2 strains shown as references.

FIG. 4 is a summary of the relationship of infectivity to immunogenicity of six of the exemplary recombinant HSV strains of the invention in test mice. FIG. 4 illustrates, for each of the six recombinants and for wild type HSV-1 and HSV-2 viruses WT17 and 186, the number of PFU required for one LD$_{50}$ by intracerebral injection. FIG. 4 also illustrates the number of PFU required for immunization against a challenge of 300 $LD_{50}$ of HSV-1 (WT17) by intracerebral injection, and the number of PFU required for immunization against a challenge of 300 $LD_{50}$ of HSV-1 (WT17) by intraperitoneal injection for each recombinant. Further, for strains D4E3, D3E2 and D5E1, FIG. 4 shows the number of PFU required for immunization against a challenge of 300 $LD_{50}$ of HSV-2 (186) by intracerebral injection.

The foregoing Examples 3 and 4 illustrate that test animals vaccinated with exemplary recombinant strains of the invention are immune to extremely high challenge doses of both HSV-1 and HSV-2, whether inoculation is effected by the intraperitoneal, intracerebral or subcutaneous route. The results are especially striking in view of the fact that challenge can be by way of the extremely sensitive intracerebral route, as well as by the intraperitoneal route.

The foregoing further illustrates that immunity is retained for at least 120 days, which is about one-quarter of the life span of the mice used in the test.

EXAMPLE 5

Latency

One characteristic of a useful vaccine is the vaccine's tendency to disappear from the host after the production of neutralizing antibodies is induced.

A series of tests of the recombinant strains D1E1, D4E3, and D5E1 were conducted wherein the latency of these recombinants were compared to HSV-1 strain KOS and HSV-2 strain 186, and wild type HSV-1 SC16 (syn+ and syn), using male and female strain 1 outbred mice. The tests utilized the mouse ear model described in Hill, "Mechanisms Involved in Recurrent Herpes Simplex" from Andre, J. et al., ed., *Human Herpesvirus and Interdisciplinary Perspective,* Elsevier, New York 1981 at pages 241–244, the disclosure of which is hereby incorporated by reference.

The tests carried out for each virus strain were divided into two groups. In the first group, clinical observations, isolation and titration of virus from skin and from ganglia were conducted during primary infection in the skin of the ear. The purpose of these tests was to determine the pattern of the disease and the ability of the virus to grow at the site of inoculation, and in the ganglia. In the second group of tests, conducted after primary infection, the following parameters were measured: latent infection in ganglia, stimulation of active infection in ganglia, induction of recurrent clinical disease, presence and persistence of neutralizing antibody, and resistance to secondary infection in the skin.

In all tests, the KOS, 186 and SC16 virus strains were inoculated at $10^4$ PFU per mouse, while the recombinant strains were inoculated at $10^5$ PFU per mouse, except as indicated below. The results are given in the following Tables VIII through XVII. The following explanatory references, the disclosures of which are hereby incorporated by reference, are cited in connection with some of the tables:

1. Hill, T. J. et al., "Acute and Recurrent Infection with Herpes Simplex Virus in the Mouse: A Model for Studying Latency and Recurrent Disease", *J. Gen. Virol.* 28:341–353 (1975)
2. Hill, T. J. et al., "Isolation of Herpes Simplex from the Skin of Clinically Normal Mice During Latent Infection", *J. Gen. Virol.* 47:205–207 (1980)
3. Hill, T. J. et al., "Trauma to the Skin Causes Recurrence of Herpes Simplex in the Mouse", *J. Gen. Virol.* 39:21–28 (1978)

SC16 virus is described in the foregoing Hill et al. articles.

TABLE VIII
CLINICAL SIGNS DURING PRIMARY INFECTION.

| VIRUS STRAIN | NUMBER OF MICE | % OF ANIMALS WITH | | | |
|---|---|---|---|---|---|
| | | NO SIGNS | INFLAMMATION ALONE | CNS SIGNS | DEATH |
| KOS | 80 | 73 | 23 | 4 | — |
| 186 | 109 | 30 | 13 | 34 | 23 |
| D1E1 | 189 | 35 | 65 | — | — |
| D4E3 | 152 | 47 | 53 | — | — |
| D5E1 | 196 | 42 | 58 | — | — |

TABLE IX
ISOLATION OF HSV FROM SKIN AND GANGLIA DURING PRIMARY INFECTION
(References 1 and 2)

| VIRUS STRAIN | TISSUE | DAYS AFTER INFECTION | | | | | | | |
|---|---|---|---|---|---|---|---|---|---|
| | | 1 | 2 | 3 | 4 | 5 | 6 | 7 | 8 |
| KOS | SKIN | 2/5 | 4/5 | 1/5 | 0 | 0 | 0 | 0 | 0 |
| | GANGLIA | 0/5 | → | → | → | → | → | → | → |
| 186 | SKIN | 0/5 | 2/5 | 1/5 | 3/5 | 2/5 | 1/5 | 1/5 | 0/5 |
| | GANGLIA | 0/5 | 0/5 | 0/5 | 1/5 | 3/5 | 2/5 | 3/5 | 2/5 |

TABLE X
ISOLATION OF HSV FROM SKIN AND GANGLIA DURING PRIMARY INFECTION
(References 1 and 2)

| VIRUS STRAIN | TISSUE | DAYS AFTER INJECTION | | | | | | |
|---|---|---|---|---|---|---|---|---|
| | | 1 | 2 | 3 | 4 | 5 | 6 | 7 |
| D1E1 | SKIN | 5/5 | 9/10 | 3/10 | 0/5 | → | → | → |
| | GANGLIA | 0/5 | → | → | → | → | → | → |
| D4E3 | SKIN | 5/5 | 5/5 | 1/5 | 0/5 | → | → | → |
| | GANGLIA | 0/5 | → | → | → | → | → | → |
| D5E1 | SKIN | 1/5 | 0/5 | → | → | → | → | → |
| | GANGLIA | 0/5 | → | → | → | → | → | → |

TABLE XI
TITRES OF HSV IN SKIN DURING PRIMARY INFECTION
(Reference 2)

| VIRUS STRAIN | $LOG_{10}$ GEOMETRIC MEAN TITER ON DAYS AFTER INFECTION | | | | | | |
|---|---|---|---|---|---|---|---|
| | 1 | 2 | 3 | 4 | 5 | 6 | 7 |
| KOS | 2.1 | 2 | 4.1 | — | — | — | — |
| 186 | — | 1.9 | 2.4 | 1.4 | 3.3 | 1.3 | 3.8 |
| D1E1 | 2.2 | 1.8 | 1.4 | — | — | — | — |
| D4E3 | 1.9 | 2.0 | 1.6 | — | — | — | — |
| D5E1 | 1.5 | — | — | — | — | — | — |

TABLE XII
ISOLATION OF HSV FROM GANGLIA DURING "LATENT INFECTION"
(References 1 and 2)

| VIRUS STRAIN | DOSE pfu/MOUSE | POSITIVE ISOLATION/NUMBER TESTED | |
|---|---|---|---|
| | | 4 DAY CULTURE | CO-CULTIVATION |
| KOS | $5 \times 10^5$ | | |
| 186 | $1 \times 10^4$ | 17/26 | |
| | $1 \times 10^3$ | 5/9 | Not Done |
| | $1 \times 10^2$ | 6/8 | |
| | $1 \times 10^1$ | 2/8 | |
| D1E1 | | 0/40 | 0/40 |
| D4E3 | | 0/40 | 0/37 |
| D5E1 | | 0/37 | 0/25 |

TABLE XIII
INCIDENCE OF CLINICAL RECURRENT DISEASE AFTER STRIPPING THE SKIN WITH CELLOPHANE TAPE (Reference 3)

| VIRUS STRAIN | CLINICAL DISEASE/NUMBER TESTED |
|---|---|
| KOS | |
| 186 | 0/30 |
| D1E1 | 0/20 |
| D4E3 | 0/24 |
| D5E1 | 0/40 |
| SC16 | 11/82 |
| UN-INFECTED | 0/23 |

TABLE XIV
ISOLATION OF INFECTIONS HSV FROM GANGLIA AFTER APPLICATION OF XYLENE TO EAR.
(Reference 3)

| VIRUS STRAIN | POSITIVE ISOLATION NUMBER TESTED ON DAYS AFTER APPLICATION | |
|---|---|---|
| | 1 | 2 |
| KOS | | |
| 186 | 1/6 | 0/6 |
| D1E1 | 0/10 | 0/8 |
| D4E3 | 0/10 | 0/9 |
| D5E1 | 0/19 | 0/20 |
| SC16 | 2/44* | 5/43 |

*In "Bristol" mice

TABLE XV
NEUTRALIZATION OF HOMOLOGOUS VIRUS BY SERUM OF ANIMALS INFECTED 2 WEEKS PREVIOUSLY WITH RECOMBINANT STRAINS.

| INFECTING VIRUS STRAIN | % NEUTRALIZATION AT FINAL CONCENTRATION OF SERUM | | | | |
|---|---|---|---|---|---|
| | 1/8 | 1/16 | 1/32 | 1/64 | 1/128 |
| D1E1 | 98 | 87 | 69 | 49 | 41 |
| D4E3 | 24 | 0 | → | → | → |
| D5E1 | 71 | 21 | 4 | 0 | → |
| SC16* | 95 | 87 | 70 | 50 | 30 |

*In "Bristol" mice.

TABLE XVI
CLINICAL SIGNS DURING PRIMARY INFECTION WITH HSV/SC16-SYN

| VIRUS DOSE PFU/MOUSE | NUMBER OF MICE | % OF ANIMALS WITH | | | |
|---|---|---|---|---|---|
| | | NO SIGNS | INFLAMMATION ALONE | CMS SIGNS | DEATH |
| $1 \times 10^5$ | 16 | — | 60 | 31 | — |
| $1 \times 10^6$ | 16 | — | 44 | 56 | 1 |
| $1 \times 10^7$ | 17 | 6 | 6 | 65 | 29 |

TABLE XVII

| CLINICAL SIGNS AFTER INFECTION WITH HSV1/SC16-syn | | | | | | |
|---|---|---|---|---|---|---|
| | CHALLENGE | NUMBER | % OF ANIMALS WITH | | | |
| PREVIOUS INOCULATION | DOSE pfu/mouse | OF MICE | NO SIGNS | INFLAMMATION ALONE | CNS SIGNS | DEATH |
| MOCK | $10^6$ | 25 | 16 | 44 | 40 | 0 |
| INFECTION | $10^7$ | 24 | 8 | 29 | 58 | 4 |
| $5 \times 10^5$ pfu $D_4E_3$ | $10^6$ | 21 | 100 | 0 | 0 | 0 |
| | $10^7$ | 20 | 90 | 10 | 0 | 0 |

The foregoing Examples and disclosure illustrate that the intertypic (HSV-1×HSV-2) recombinant strains of the invention exhibit the characteristics of immunogenicity, avirulence, lack of a tendency to revert to virulence, and lack of persistence in the host following immunization. Further, the intertypic recombinants are effective against both wild-type HSV-1 and HSV-2.

Immunization Routes, Dosages and Indications

A human host is preferably inoculated with a vaccine comprising a solution of an immunity-inducing dose of one or more of the live intertypic (HSV-1×HSV-2) vaccinal recombinant strains of the invention by the parenteral route, preferably by intramuscular or subcutaneous injection. Also, inoculation can be effected by surface scarification, or by inoculation of a body cavity. Typically, one inoculation of between about 10 and 10,000 PFU, as measured in human diploid cell strains, is sufficient to effect immunization of a human host.

Indications for vaccination include:

(a) a lack of immunity in the face of a high probability of natural infection; or (b) a lack of immunity and a likelihood that the subject will become immunologically compromised because of immunosuppressive therapy in the immediate or not too distant future.

In addition to utility in immunizing a human host against wild-type HSV-1 and HSV-2, intertypic (HSV-1×HSV-2) recombinant strains of the invention are believed to have utility in treating a subject infected with wild-type HSV-1 and HSV-2. Treatment can be effected using similar dosages and routes of administration as used in immunization, described above.

The foregoing detailed description is given for clearness of understanding only, and no unnecessary limitations are to be understood therefrom, as modifications within the scope of the invention will be obvious to those skilled in the art.

We claim:

1. A live viral vaccine which is effective against wild-type HSV-1 and HSV-2, said vaccine comprising an immunity-including dose of at least one vaccinal intertypic (HSV-1×HSV-2) recombinant virus strain, said strain being prepared by the method comprising the steps of:

(a) crossing two prototypical HSV-1 and HSV-2 parental virus strains to obtain recombinant progeny, said parental strains having distinguishing genetic markers such that said recombinant progeny can be distinguished from said parental strains on the basis of said markers, at least one of said parental strains being distinguished by a temperature sensitive phenotype;

(b) identifying recombinant progeny distinguished by a temperature resistant phenotype;

(c) isolating said recombinant progeny of (b) from said parental strains and from recombinant progeny having a temperature sensitive phenotype; and, (d) selecting from said temperature resistant progeny those strains which exhibit vaccinal characteristics with respect to wild-type HSV-1 and HSV-2.

2. The vaccine of claim 1 wherein said selection is effected by empirical determination of avirulence, stability with respect to avirulence, immunogenicity, and latency, with respect to wild-type HSV-1 and HSV-2.

3. A method of immunizing a human host against wild-type HSV-1 and HSV-2, said method comprising the step of inoculating said host with an immunity including dose of a live viral vaccine which comprises at least one vaccinal intertypic (HSV-1×HSV-2) recombinant virus strain prepared by the steps of:

(a) crossing two prototypical HSV-1 and HSV-2 parental virus strains to obtain recombinant progeny, said parental strains having distinguishing genetic markers such that said recombinant progeny can be distinguished from said parental strains on the basis of said markers, at least one of said parental strains being distinguished by a temperature sensitive phenotype;

(b) identifying recombinant progeny distinguished by a temperature resistant phenotype;

(c) isolating said recombinant progeny of (b) from said parental strains and from recombinant progeny having a temperature sensitive phenotype; and, (d) selecting from said progeny those strains which exhibit vaccinal characteristics with respect to wild-type HSV-1 and HSV-2.

4. The method of claim 3 wherein said selection is effected by empirical determination of avirulence, stability with respect to avirulence, immunogenicity, and latency, with respect to wild-type HSV-1 and HSV-2.

5. The method of claim 3 or 4 wherein said host lacks immunity to said wild-type HSV-1 and HSV-2 and faces a high probability of natural infection by either or both of said wild-type HSV-1 and HSV-2.

6. The method of claim 3 or 4 wherein said host lacks immunity to said wild-type HSV-1 and HSV-2 and is likely to become immunologically compromised.

7. The method of claim 3 or 4 wherein said host lacks immunity to said wild-type HSV-1 and HSV-2 and is likely to become immunologically compromised as a result of immunosuppressive therapy.

8. A method of immunizing a human host against virulent HSV-1 and HSV-2, which method comprises the step of inoculating said host with a live viral vaccine which comprises as an effective ingredient at least one stable, avirulent intertypic (HSV-1×HSV-2) recombinant virus strain selected from the group consisting of the strains designated A5C (ATCC No. VR 2019), D4E1 (ATCC No. VR 2020), D4E3 (ATCC No. VR 2021), C7D (ATCC No. VR 2022), D4E2 (ATCC No.

VR 2023), C5D (ATCC No. VR 2024), D5E1 (ATCC No. VR 2025) and D1E1 (ATCC No. VR 2026).

9. The method of claim 8 wherein said recombinant strain comprises the strain designated A5C (ATCC No. VR 2019).

10. The method of claim 8 wherein said recombinant strain comprises the strain designated D4E1 (ATCC No. VR 2020).

11. The method of claim 8 wherein said recombinant strain comprises the strain designated D4E3 (ATCC No. VR 2021).

12. The method of claim 8 wherein said recombinant strain comprises the strain designated C7D (ATCC No. VR 2022).

13. The method of claim 8 wherein said recombinant strain comprises the strain designated D3E2 (ATCC No. VR 2023).

14. The method of claim 8 wherein said recombinant strain comprises the strain designated C5D (ATCC No. VR 2024).

15. The method of claim 8 wherein said recombinant strain comprises the strain designated D5E1 (ATCC No. VR 2025).

16. The method of claim 8 wherein said recombinant strain comprises the strain designated D1E1 (ATCC No. VR 2026).

17. A method of immunizing a human host against virulent HSV-1 and HSV-2, which method comprises the step of inoculating said host with a live viral vaccine which comprises as an effective ingredient at least one stable, avirulent, intertypic (HSV-1×HSV-2) recombinant strain having the identifying characteristics of a strain selected from the group consisting of A5C (ATCC No. VR 2019), D4E1 (ATCC No. VR 2020), D4E3 (ATCC No. VR 2021), C7D (ATCC No. VR 2022), D3E2 (ATCC No. VR 2023), C5D (ATCC No. VR 2024), D5E1 (ATCC No. VR 2025) and D1E1 (ATCC No. VR 2026).

18. A method of immunizing a human host against virulent HSV-1 and HSV-2, which method comprises the step of inoculating said host with a live viral vaccine which comprises as an effective ingredient at least one stable, avirulent, intertypic (HSV-1×HSV-2) recombinant strain having the BamH1 and Kpn1 fingerprints shown in FIGS. 1 and 2.

19. A live viral vaccine against virulent HSV-1 and HSV-2 which comprises as an effective ingredient an immunity-inducing dose of at least one stable, avirulent, intertypic (HSV-1×HSV-2) recombinant virus strain selected from the group consisting of the strains designated A5C (ATCC No. VR 2019), D4E1 (ATCC No. VR 2020), D4E3 (ATCC No. VR 2021), C7D (ATCC No. VR 2022), D5E2 (ATCC No. VR 2023), C5D (ATCC No. VR 2024), D5E1 (ATCC No. VR 2025) and D1E1 (ATCC No. VR 2026).

20. The vaccine of claim 19 wherein said recombinant strain comprises the strain designated A5C (ATCC No. VR 2019).

21. The vaccine of claim 19 wherein said recombinant strain comprises the strain designated D4E1 (ATCC No. VR 2020).

22. The vaccine of claim 19 wherein said recombinant strain comprises the strain designated D4E3 (ATCC No. VR 2021).

23. The vaccine of claim 19 wherein said recombinant strain comprises the strain designated C7D (ATCC No. VR 2022).

24. The vaccine of claim 19 wherein said recombinant strain comprises the strain designated D3E2 (ATCC No. VR 2023).

25. The vaccine of claim 19 wherein said recombinant strain comprises the strain designated C5D (ATCC No. VR 2024).

26. The vaccine of claim 19 wherein said recombinant strain comprises the strain designated D5E1 (ATCC No. VR 2025).

27. The vaccine of claim 19 wherein said recombinant strain comprises the strain designated D1E1 (ATCC No. VR 2026).

28. A method of treating a human subject infected with wild-type HSV-1 or HSV-2, or both, said method comprising the step of administering to said subject an effective dose of the vaccine of claim 1, 2, 19 or 30.

29. A live viral vaccine against virulent HSV-1 and HSV-2 which comprises as an effective ingredient at least one stable, avirulent, intertypic (HSV-1×HSV-2) recombinant strain having the BamH1 and Kpn1 fingerprints shown in FIGS. 1 and 2.

30. The vaccine of claim 1 comprising between about 10 and 10,000 plaque-forming units of said vaccinal strain.

31. The method of claim 3 wherein said vaccine comprises between about 10 and 10,000 plaque-forming units of said vaccinal strain.

* * * * *